US008017581B1

(12) United States Patent
Martinez et al.

(10) Patent No.: US 8,017,581 B1
(45) Date of Patent: Sep. 13, 2011

(54) MSH-AGONIST TRIPEPTIDE CONJUGATES

(75) Inventors: Jean Martinez, Caux (FR); Pascal Verdie, Saint Mathieu de Treviers (FR); Pascaline Dubs, Montpellier (FR); Anne-Marie Pinel, Toulouse (FR); Gilles Subra, Juvignac (FR)

(73) Assignees: Centre National de la Recherche Scientifique (CNRS), Paris (FR); Institut Europeen de Biologie Cellulaire, Ramonville St. Ange (FR); Universite de Montpellier I, Montpellier (FR); Universite Montpellier II, Montpellier (FR)

( * ) Notice: Subject to any disclaimer, the term of this patent is extended or adjusted under 35 U.S.C. 154(b) by 980 days.

(21) Appl. No.: 11/596,041

(22) PCT Filed: May 10, 2005

(86) PCT No.: PCT/FR2005/001165
§ 371 (c)(1),
(2), (4) Date: Jun. 28, 2007

(87) PCT Pub. No.: WO2005/116067
PCT Pub. Date: Dec. 8, 2005

(30) Foreign Application Priority Data

May 11, 2004 (FR) ..................................... 04 05069
Oct. 22, 2004 (FR) ..................................... 04 11276

(51) Int. Cl.
*A61K 38/00* (2006.01)
(52) U.S. Cl. .......................................... 514/18; 530/330
(58) Field of Classification Search ........................ None
See application file for complete search history.

(56) References Cited

U.S. PATENT DOCUMENTS

| 5,674,839 A | 10/1997 | Hruby et al. |
| 5,714,576 A | 2/1998 | Hruby et al. |
| 5,786,332 A | 7/1998 | Girten et al. |
| 5,830,994 A | 11/1998 | D'Hinterland et al. |
| 6,054,556 A | 4/2000 | Hruby et al. |
| 6,245,342 B1 | 6/2001 | Golz-Berner et al. |
| 6,337,315 B1 | 1/2002 | Mahe et al. |
| 2004/0010010 A1 | 1/2004 | Ebetino et al. |
| 2005/0187164 A1 | 8/2005 | Pinel |

FOREIGN PATENT DOCUMENTS

| EP | 0 669 938 B1 | 9/1995 |
| EP | 0 949 902 B1 | 10/1999 |
| EP | 0 972 522 B1 | 1/2000 |
| FR | 2 810 323 A1 | 12/2001 |
| WO | WO 95/08564 A1 | 3/1995 |
| WO | WO 98/25584 A1 | 6/1998 |
| WO | WO 01/98362 A2 | 12/2001 |
| WO | WO 02/085925 A2 | 10/2002 |
| WO | WO 03/064458 A2 | 8/2003 |
| WO | WO 03/095474 A2 | 11/2003 |
| WO | WO 2004/099237 A1 | 11/2004 |
| WO | WO 2004/110341 A2 | 12/2004 |
| WO | WO 2005/116068 A1 | 12/2005 |

OTHER PUBLICATIONS

Haskell-Luevano et al., Peptides, 1996, vol. 17, No. 6, pp. 995-1002.*
Al-Obeidi et al., "Synthesis and Biological Activities of Fatty Acid Conjugates of a Cyclic Lactam α-Melanotropin," J. Med. Chem., 1992, 34:118-123.
Hadley et al., "Biological Activities of Melanotropic Peptide Fatty Acid Conjugates," Pigment Cell Research, 1991, 4:180-185.
Haskell-Luevano et al., "Characterization of Melanocortin NDP-MSH Agonist Peptide Fragments at the Mouse Central and Peripheral Melanocortin Receptors," J. Med. Chem., 2001, 44, 2247-2252.
Haskell-Luevano et al., "Discovery of Prototype Peptidomimetic Agonists at the Human Melanocortin Receptors MC1R and MC4R," J. Med. Chem., 1997, 40:2133-2139.
Haskell-Luevano et al., "Truncation Studies of α-Melanotropin Peptides Identify Tripeptide Analogues Exhibiting Prolonged Agonist Bioactivity," Peptides, 1996, 17(6), 995-1002.
Hiltz et al., "Alpha-MSH Peptides Inhibit Acute Inflammation and contact Sensitivity," Peptides, 1990, 11:979-982.
Holder et al., "Characterization of aliphatic, cyclic, and aromatic N-terminally 'capped' His-D-Phe-Arg-Trp-$NH_2$ tetrapeptides at the melanocortin receptors," European Journal of Pharmacology, 2003, 462:41-52.
Holder et al., "Structure-Activity Relationships of the Melanocortin Tetrapeptide Ac-His-D-Phe-Arg-Trp-$NH_2$ at the Mouse Melanocortin Receptors. 4. Modifications at the Trp Position," J. Med. Chem., 2002, 45:5736-5744.
Holder et al., "Structure-Activity Relationships of the Melanocortin Tetrapeptide Ac-His-D-Phe-Arg-Trp-NH2 at the Mouse Melanocortic Receptors. 1. Modifications at the His Position," J. Med. Chem., 2002, 45:2801-2810.
Hruby et al., "Alpha-Melanotropin: The Minimal Active Sequence in the Frog Skin Bioassay," J. Med. Chem., 1987, 30:2126-2130.
Jacubovich et al., "Tumour-associated Antigens in Culture Medium of Malignant Melanoma Cell Strains," Cancer Immunol. Immunother., 1979, 7:59-64.

(Continued)

*Primary Examiner* — Christopher R. Tate
*Assistant Examiner* — Roy Teller
(74) *Attorney, Agent, or Firm* — Foley & Lardner LLP

(57) ABSTRACT

The invention relates to a tripeptide conjugate having general formula I, A-AA1-AA2-AA3-$NH_2$, wherein A represents the radical corresponding to a monocarboxylic acid with general formula II, HOOC—R, in which: R represents a linear or branched aliphatic radical at $C_1$-$C_{24}$, which is optionally substituted by a hydroxyl group and which can comprise one or more unsaturations, preferably between 1 and 6 unsaturations, lipoic acid or the reduced form thereof, dihydrolipoic acid, N-lipoyllysine, or phenylbutyric acid; and AA1, AA2 and AA3, which may be identical or different, represent independently of each other an amino acid selected from His, Phe, Ala, Arg, Lys, Orn, Trp, Nap, Tpi and Tic, on the condition that at least one of AA1, AA2 or AA3 represent Phe, preferably Dphe in the form of enantiomers or diastereoisomers and mixtures thereof, including racemic mixtures.

8 Claims, No Drawings

OTHER PUBLICATIONS

Koikov et al., "Analogs of sub-nanomolar hMC1R agonist LK-184 [Ph(CH2)3CO-His-D-Phe-Arg-Trp-NH2]. An additional binding site within the human melanocortin receptor 1?", Bioorganic & Medicinal Chemistry Letters, 2004, 14:3997-4000.

Koikov et al., "Sub-Nanomolar hMC1R Agonists by End-Capping of the Melanocortin Tetrapeptide His-D-Phe-Arg-Trp-NH2," Bioorganic & Medicinal Chemistry Letters, 2003, 13:2647-2650.

Lipton, James M., "Modulation of Host Defense by the Neuropeptide alpha-MSH," Yale Journal of Biology and Medicine, 1990, 63:173-182.

Nijenhuis et al., "Discovery and in vivo evaluation of new melanocortin-4 receptor-selective peptides," Peptides, 2003, 24:271-280.

Takahama, Motohide, "α-MSH discovered in primary root of sesame seeds, and trial on remelanization of gray hairs by their extract: immunohistochemical study," Journal of Dermatological Science, Apr. 2004, (34(2), p. 148, XP002302532 & 19th Annual meeting of the Japanese Society for Investigative Dermatology, Kyoto, Japan, Apr. 14-16, 2004, one page.

Tatro et al., "Specific Receptors for alpha-Melanocyte-Stimulating Hormone Are Widely Distributed in Tissues of Rodents," Endocrinology, 1987, 121(5): 1900-1907.

Todorovic et al., "N-Terminal Fatty Acylated His-DPhe-Arg-Trp-NH2 Tetrapeptides: Influence of Fatty Acid Chain Length of Potency and Selectivity at the Mouse Melanocortin Receptors and Human Melanocytes," J. Med. Chem., 2005, 48:3328-3336.

Yasumura et al., "Establishment of Four Functional, Clonal Strains of Animal Cells in Culture," Science, 1996, 154:1186-1189.

\* cited by examiner

SEQUENCE LISTING

```
<160> NUMBER OF SEQ ID NOS: 2

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetylation
<220> FEATURE:
<223> OTHER INFORMATION: C-term NH2
```

```
<400> SEQUENCE: 1

Ser Tyr Ser Met Glu His Phe Arg Trp Gly Lys Pro Val
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetylation
<220> FEATURE:
<221> NAME/KEY: MOD_RES
<222> LOCATION: (1)..(1)
<223> OTHER INFORMATION: Nle
<220> FEATURE:
<221> NAME/KEY: MOD_RES
<222> LOCATION: (4)..(4)
<223> OTHER INFORMATION: Phe or D-Phe
<220> FEATURE:
<223> OTHER INFORMATION: C-term NH2

<400> SEQUENCE: 2

Xaa Ala His Xaa Arg Trp
1               5
```

MSH-AGONIST TRIPEPTIDE CONJUGATES

CROSS REFERENCE TO RELATED APPLICATIONS

This application is a National Stage application of PCT/FR2005/001165, filed May 10, 2005, which claims priority from French patent applications FR 0405069, filed May 11, 2004, and FR 0411276, filed Oct. 22, 2004.

The present invention relates to novel MSH-agonist tripeptide conjugates and to the therapeutic and cosmetic use thereof.

Alpha-MSH is a substance naturally produced by the human organism, known to have a very large number of physiological activities: antipyretic, anti-inflammatory and pigmenting activities.

As a mediator, alpha-MSH has specific receptors, five of which have been described and each have seven transmembrane domains. In the skin, the activities mentioned above involve the "melanocortin-1" receptor (MC-1r). The binding of alpha-MSH to said receptor induces the activation of a G protein (having a Gγs-type α-subunit) that would itself stimulate adenylyl cyclase and thus produce cyclic adenosine monophosphate (or cAMP).

The production of cAMP induces the activation of type A protein kinases which will activate, by phosphorylation, proteins capable of binding to cAMP response elements (or CREBs) at the level of the DNA of the cell's genes. This leads to the expression of mediators that then exert their effects on target cells.

In mammals, the coloration of the skin and of the hairs is due to a common category of pigments: melanins. The protection of these melanins in the skin is provided by melanocytes, which are cells located at the epidermal basal membrane and in the hair follicles. Melanin synthesis is controlled by the activity of an enzyme: tyrosinase. It is the production of this enzyme (and also that of the associated enzymes: TRP-1 & TRP-2) that is stimulated by the bonding of alpha-MSH to its MC-1 receptor. The production of melanin by tyrosinase takes place in cytoplasmic organelles: premelanosomes. Once filled with melanins, these organelles are called melanosomes and are transferred, by means of the melanocyte's dendrites, to the neighboring cells: keratinocytes. The melanin is thus distributed in the epidermis, providing browning and protection thereof.

Melanin, a natural pigment known for its free-radical-scavenging and solar-radiation-absorbing properties, is the physiological protective agent of the skin. No compound is available in dermocosmetology that can stimulate the production of this pigment in humans.

Furthermore, the mechanism of the anti-inflammatory effects of alpha-MSH has not been completely elucidated, but many experimental facts converge and lead one to think that alpha-MSH, by binding to the MC-1 receptor, inhibits the induction of NOSi (or NOS2) and of NFκB and induces the expression of the mRNA followed by the production of the anti-inflammatory cytokine IL-10. This cytokine opposes the release of inflammatory cytokines such as IL-1, IL-6, IL-8, TNF-α or IFNγ.

Keratinocytes, which constitute 95% of the cell population of the epidermis, are considered to be IL-1 reservoirs and have MC-1 receptors at their cell surface. Thus, the binding of alpha-MSH to these receptors allows a modulation of local inflammatory phenomena.

Alpha-MSH is a tridecapeptide of formula acetyl-$Ser^1$-$Tyr^2$-$Ser^3$-$Met^4$-$Glu^5$-$His^6$-$Phe^7$-$Arg^8$-$Trp^9$-$Gly^{10}$-$Lys^{11}$-$Pro^{12}$-$Val^{13}$-$NH_2$ (where Ser=serine, Tyr=tyrosine, Met=methionine, Glu=glutamic acid, His=histidine, Phe=phenylalanine, Arg=arginine, Trp=tryptophan, Gly=glycine, Lys=lysine, Pro=proline and Val=valine). A large number of scientific studies have established the active sequences of alpha-MSH, which are conventionally described as being the heptapeptide 4-10 for the melanotropic effects (Haskell-Luevano et al. *J. Med. Chem.* 1997, 40, 2133-2139) and the tripeptide 11-13 for the anti-inflammatory effects (Hiltz M. E. and Lipton J. M. *Peptides* 1990, 11, 979-982.).

Furthermore, recent studies have led various authors to file patents describing cyclized structures (Hruby et al. U.S. Pat. No. 5,674,839 & U.S. Pat. No. 6,054,556).

Moreover, the tetrapeptide $Ph(CH_2)_3CO$-His-DPhe-Arg-Trp has a very substantial activity as an alpha-MSH agonist (Koikov et al. *Bioorganic & Medicinal Chemistry Letters*, 13 (2003), pages 2647-2650). This tetrapeptide sequence has always been identified as being the minimal fragment exhibiting a biological activity and no other modification of the size of the tetrapeptide has been described or suggested to date. However, the size and the molecular weight of this tetrapeptide are still too great.

Surprisingly, the inventors have discovered that certain tripeptides palmitoylated at the N-terminal end still exhibit a significant α-MSH-agonist activity. These agonists have a very low molecular weight, are therefore easy to optimize, have a good bioavailability and are very easy to prepare.

The present invention therefore relates to a tripeptide conjugate corresponding to general formula I:

A-AA1-AA2-AA3-$NH_2$      I in which
A represents the radical corresponding to a monocarboxylic acid of general formula II:

HOOC—R      II in which R represents
- a linear or branched $C_1$-$C_{24}$ aliphatic radical, optionally substituted with a hydroxyl group, that may contain one or more unsaturations, advantageously from 1 to 6 unsaturations,
- lipoic acid or its reduced form dihydrolipoic acid, N-lipoyllysine or phenylbutyric acid, AA1, AA2 and AA3, which may be identical or different, represent, independently of one another, an amino acid chosen from His, Phe, Ala, Arg, Lys, Orn, Trp, Nap, Tpi and Tic, with the proviso that at least one of AA1, AA2 or AA3 represents Phe, advantageously DPhe,
in the form of enantiomers or of diastereoisomers, and also mixtures thereof, including racemic mixtures.

The amino acids in the tripeptide conjugate of formula (I) may have a D, L or DL configuration if this is not otherwise specified.

Thus, the tripeptide conjugates of formula (I) may contain one or more asymmetrical carbon atoms. They may therefore exist in the form of enantiomers or of diastereoisomers. These enantiomers and diastereoisomers, and also mixtures thereof, including racemic mixtures, are part of the invention.

In the context of the present invention, the term:
"Ala" is intended to mean alanine,
"Phe" is intended to mean phenylalanine,
"Trp" is intended to mean tryptophan,
"Arg" is intended to mean arginine,
"Nap" is intended to mean naphthylalanine,
"Tpi" is intended to mean tetrahydronorhaman-3-carboxylic acid, "Tic" is intended to mean tetrahydroisoquinoline-3-carboxylic acid,
"Orn" is intended to mean ornithine,
"His" is intended to mean histidine, and
"Lys" is intended to mean lysine.

It is also specified that the tripeptide conjugates mentioned above and which are the subject of the present invention are obtained in the $NH_2$-terminal form (in other words, exhibiting an amide function).

The tripeptides conjugated according to the present invention are linked in the form of salts or of esters to the acid of formula II. The conjugations according to the present invention may be carried out by reacting the acid function of the amino acid with the acid function of the acid of formula II, or it is even possible to take advantage of the presence of a hydroxyl function on the acid of formula II.

The present invention relates to all these conjugations and also to the nonfunctional conjugates. The conjugations are physical or chemical.

Advantageously, at least one of AA1, AA2 or AA3, advantageously two, is chosen from the group consisting of Arg, His or Trp.

Advantageously, AA2 represents DPhe.

Advantageously, AA2 or AA3 represents Arg.

Advantageously, AA1 represents His.

Advantageously, AA1 does not represent DPhe or Phe when AA2 represents Arg and AA3 represents Trp.

Advantageously, the acid of formula (II) is a polyunsaturated fatty acid, i.e. comprising from 1 to 6 unsaturations. Even more advantageously, it is an omega-3 acid.

Among these omega-3 acids, mention may in particular be made of α-linolenic acid, cervonic acid, timnodonic acid and pinolenic acid. Cervonic acid, timnodonic acid and pinolenic acid are also known under the respective names 4,7,10,13,16,19-docosahexaenoic acid (DHA), 5,8,11,14,17-eicosapentaenoic acid (EPA) and 5,9,12-octadecatrienoic acid.

When A represents a monocarboxylic acid radical of general formula (II), it may advantageously be chosen from acetic acid, myristic acid, palmitic acid, hydroxydecenoic acid and decenoic acid, and in particular trans-10-hydroxy-A2-decenoic acid and trans-oxo-9-decen-2-oic acid.

Advantageously, the acid of formula (II) is an acid chosen from lipoic acid (Lip) or its reduced form dihydrolipoic acid, N-lipoyllysine or phenylbutyric acid (Pbu).

Advantageously, A represents the radical corresponding to palmitic acid (Palm).

Among the tripeptide conjugates of the invention, mention may be made of the tripeptide conjugates chosen from the group consisting of:
a) A-His-DPhe-Arg-$NH_2$,
b) A-His-DPhe-Trp-$NH_2$,
in which A has the definition indicated above.

Among the tripeptide conjugates of the invention, mention may be made of the tripeptide conjugates chosen from the group consisting of:
1) Palm-His-DPhe-Arg-$NH_2$
2) Palm-His-DPhe-Trp-$NH_2$,
3) Pbu-His-DPhe-Arg-$NH_2$,
4) Lip-His-DPhe-Arg-$NH_2$.

The tripeptide conjugates which are the subject of the present invention can be obtained either advantageously by conventional chemical synthesis, or by enzymatic synthesis, according to any methods known to those skilled in the art.

The present invention also relates to a cosmetic, dermatological or pharmaceutical composition or a food supplement comprising a tripeptide conjugate according to the present invention and, optionally, a cosmetically or pharmaceutically acceptable excipient.

The tripeptide conjugates may be administered topically for their cosmetic or pharmaceutical use. They may also be used in food supplements, in other words, in the nutraceutical field by oral administration.

The tripeptide conjugates according to the invention are preferably administered topically.

The cosmetic, pharmaceutical or dermatological composition may be in the forms that are usually known for this type of administration, i.e., in particular, lotions, foams, gels, dispersions, sprays, sera, masks, body milks, ointments, solutions, emulsions, gels or creams, for example, with excipients that make it possible in particular to penetrate the skin in order to improve the properties and the accessibility of the active ingredient. These compositions generally contain, in addition to the tripeptide conjugate according to the present invention, a physiologically acceptable medium, generally based on water or on a solvent, for example alcohols, ethers or glycols. They may also contain surfactants, preserving agents, stabilizers, emulsifiers, thickeners, other active ingredients that result in a supplementary or, optionally, synergistic effect, trace elements, essential oils, fragrances, colorants, collagen, chemical or inorganic screening agents, moisturizers or thermal spring waters.

In the topical cosmetic composition, the tripeptide conjugate according to the invention may be present at a concentration of between $10^{-8}$ M and $10^{-3}$ M, advantageously between $10^{-7}$ M and $10^{-5}$ M.

The present invention also relates to a tripeptide conjugate according to the present invention or a pharmaceutical composition according to the present invention, for its use as a medicament, advantageously for use in treating cancer, in healing chronic wounds and lesions in diabetics, varicose ulcers or surgical wounds, in treating or preventing stretchmarks, allergies, in particular skin allergies, inflammatory reactions, melanogenesis disorders, atopic dermatitis, eczema, psoriasis, vitiligo, erythema, and in particular photo-induced erythema, inflammatory alopecia or asthma, or in treating obesity.

It also relates to the use of a tripeptide conjugate according to the present invention, for the manufacture of a medicament for use in treating cancer, in healing chronic wounds and lesions in diabetics, varicose ulcers or surgical wounds, in treating or preventing stretchmarks, allergies, in particular skin allergies, inflammatory reactions, melanogenesis disorders, atopic dermatitis, eczema, psoriasis, vitiligo, erythema, and in particular photo-induced erythema, inflammatory alopecia or asthma, or in treating obesity.

The present invention also relates to the use of a cosmetic composition according to the present invention, as a melanotropic and/or anti-erythematous agent, for accelerating epidermal melanization, for obtaining natural skin tanning, for the curative and preventive treatment of wrinkles on the face, neck and hands, or for providing complete protection against ultraviolet (UVA-UVB) solar radiation.

Finally, the present invention relates to a cosmetic treatment process for accelerating epidermal melanization, for obtaining natural skin tanning, for the curative and preventive treatment of wrinkles on the face, neck and hands, or for providing complete protection against ultraviolet (UVA-UVB) solar radiation, comprising the application to the skin of a cosmetic composition according to the present invention.

The following examples are given by way of nonlimiting indication.

EXAMPLE 1

Preparation of 2 Tripeptides According to the Invention

The chemical products used are the following:

The amino acids protected at the N-terminal end with an α-Fmoc, Fmoc-Arg(Pbf)-OH, Fmoc-D-Arg(Pbf)-OH, Fmoc-His(TrT)-OH, Fmoc-D-His(Trt)-OH, Fmoc-Phe-OH, Fmoc-D-Phe-OH, Fmoc-Trp(Boc)-OH or Fmoc-D-Trp (Boc)-OH group were purchased from SENN chemicals and from Advanced Chemtech.

The coupling agent HBTU (2-(1-H-benzotriazol-1-yl)-1, 1,3,3-tetramethyluronium hexafluorophosphate) was purchased from SENN chemicals.

N,N-Dimethylformamide (DMF), dichloromethane (DCM), methanol, acetonitrile, ethyl ether, trifluoroacetic acid (TFA), piperidine and acetic anhydride were purchased from Riedel de Haën, Carlo Erba or Acros organics and used without purification.

Acetyl chloride, acetic anhydride, N,N-diisopropylethylamine, triisopropylsilane, benzenesulfonyl chloride, 3-pyridinepropionic acid, butanoic acid, hexanoic acid, 3-cyclohexylpropionic acid, propionic acid, benzoic acid, trans-cinnamic acid, palmitic acid, p-toluenesulfonyl chloride, 3,3'-diphenylpropionic acid, hexanoic acid, myristic acid, adamantylcarboxylic acid, indol-3-acetic acid, (2-pyrid-3-yl) thiazole-4-carboxylic acid, 3-thio-phenacetic acid, 2-thiophenacetic acid, 2-benzimidazole-propionic acid, 4-biphenylacetic acid, 4-pyridylacetic acid, α-methyl-p-(2-thienoyl)phenylacetic acid (suprofen) and α-methyl-4-(2-methylpropyl)benzeneacetic acid (ibuprofen) were purchased from Aldrich or Avocado. All the chemical reagents and products were of ACS quality and they were used without other purification.

The D-series Rink amide Synphase polyamide lanterns and the D-series Synphase hydroxy trityl polystyrene lanterns were provided by Mimotopes, Pty.

The [$^{125}$I]-NDP-MSH used for competition binding assays was prepared according to a procedure described in the article by Tatro et al. (*Endocrinology* 1987, 121, 1900).

The solid-phase peptide synthesis was carried out using the Fmoc strategy on an ACT496Ω automated synthesizer. Each well was filled with 150 mg of PS-Rink amide resin. The resin was left to swell for 30 minutes in DCM. The deprotection and coupling steps were carried out until the desired sequences were synthesized. For the coupling step, three solutions were successively added to the reaction cuvettes: 400 μl of a 0.5 M solution of amino acid protected at the N-terminal end with an Fmoc group in N-methylpyrrolidone; 400 μl of a 0.5 M solution of N-methylmorpholine in DMF and 400 μl of a 0.5 M solution of HBTU in DMF. The coupling time was 90 min. The 20 min deprotection step was carried out using 1.2 ml of DMF/piperidine (80/20 solution, v/v). Five washes with 1.5 ml were used between the steps, including twice with DMF, once with DCM, once with methanol and once with DMF.

The side-chain deprotection and the peptide cleavage were carried out for 2 hours in the 96-reactor block of the automated device, using 1.5 ml of cleavage cocktail (trifluoroacetic acid/water/triisopropylsilane, 95/2.5/2.5, v/v/v) per well. After removal of the resin by filtration, the cleavage cocktail was concentrated in a Jouan RC10-10 vacuum centrifuge. The peptides were precipitated from diethyl ether and converted to pellet by centrifugation, and the ether was removed. This operation of separation by settling out was repeated with fresh diethyl ether. The crude peptide was solubilized in acetonitrile/water (50/50, v/v) containing 0.1% of TFA. The samples were then frozen at −80° C. and lyophilized. This process was repeated twice.

A sample of 50 mg of crude peptide was purified by reverse-phase liquid chromatography using the Waters Deltaprep system with a double wavelength detector (214 and 254 nm) and a deltapack $C_{18}$ cartridge using the same solvent system as for the analysis.

The simple peptides were analyzed by reverse-phase HPLC and LC/MS. 500 μl of acetonitrile/water (50/50, v/v) containing 0.1% of TFA were distributed onto the lyophilized compounds. 10 μl were taken from each tube for the HPLC and LC/MS ESI+ analysis.

The HPLC analyses were carried out on a Waters Alliance 2690 HPLC system with a Waters 996 photodiode array detector and a Merck Chromolith Speed ROD, 50×4.6 mm, C18 column. A flow rate of 5 ml/min and a gradient of 100% of B to 100% of C over 3 min were used (eluant B, water/0.1% TFA; eluant C, acetonitrile/0.1% TFA). The estimations of purity are based on the percentage surface area of the peaks detected at 214 nm.

The LC/MS system consisted of a Waters Alliance 2690 HPLC coupled to a Micromass Platform II spectrometer (electrospray ionization mode, ESI+). All the analyses were carried out using a Waters Symmetry C18, 3.5 μm, 2.1×30 mm column. A flow rate of 600 μl/min and a gradient of 100% of B to 100% of C over 3 min were used (eluant B, water/0.1% TFA; eluant C, acetonitrile/0.1% TFA).

The positive electrospray ionization mass spectra were acquired at a solvent flow rate of 100 ml/min. Nitrogen was used both as the spraying gas and as the drying gas. The data were acquired in a reading mode of m/z 400 to 1400 in intervals of $0.1^{-s}$; 10 readings were added to produce the final spectrum.

The molecular weights of all the compounds were calculated using monoisotopic masses (C=12.000, H=1.007, N=14.003, O=15.994, S=31.972).

The results for the two tripeptides synthesized are given in table 1 below:

TABLE 1

Analytical results of the tripeptide synthesis

| No. of peptide conjugate according to the invention | A | AA1 | AA2 | AA3 | | % purity | Molecular weight |
|---|---|---|---|---|---|---|---|
| 1 | Palm | His | DPhe | Arg | $NH_2$ | 92 | 695.4 |
| 2 | Palm | His | DPhe | Trp | $NH_2$ | 97 | 725.4 |

EXAMPLE 2

Biological Properties of the 2 Tripeptide Conjugates According to the Present Invention The M4Be human cell line (Jacubovich et al. *Cancer Immunol. Immunother.* 1979, 7, 59-64), a melanocyte cell line capable of producing melanins, was used in this study to determine the $EC_{50}$ values.

The cells were maintained in Dulbecco's modified Eagle medium, with 10% of FCS, 1 mM of glutamine, 100 U/ml of penicillin and $10^{-4}$ g/ml of streptomycin. All the cell lines were maintained at 37° C. in a 5% $CO_2$ atmosphere, and the cell culture media were renewed every two days. The cells were plated onto a 96-well plate (Nunc, Roskilde, Denmark) 24 hours before contact with the peptides.

The Cloudman S91 mouse melanoma cell line (Yasumara et al. *Science*. 154, pages 1186-1189) was used for the preliminary screening. The cells were maintained in HAM F10 with 10% of horse serum, 2% of fetal calf serum (FCS), 1 mM of glutamine, 100 U/ml of penicillin and $10^{-4}$ g/ml of streptomycin (Eurobio, Les Ulis, France). All the cell lines were maintained at 37° C. in a 5% $CO_2$ atmosphere, and the cell culture media were renewed every two days. The cells were plated out onto a 96-well plate (Nunc, Roskilde, Denmark) 24 hours before contact with the peptides.

cAMP Measurement:

Briefly, the cells plated out the day before were incubated for 1 hour with $10^{-4}$ M of adenine (Sigma) and then for 10 minutes in Krebs Ringer Hepes medium with $10^{-4}$ M of isobutyl-1-methylxanthine (Sigma), $10^{-4}$ M of 4-[(3-butoxy-4-methoxyphenyl)methyl]-2-imidazolidinone (Calbiochem) and tripeptides according to the invention, at $10^{-7}$ M.

After this period of time, cell lysis was carried out according to the manufacturer's protocol.

The cAMP content was measured using a competition binding assay kit (RPN225, Amersham Pharmacia Biotech) according to the manufacturer's instructions. Each independent experiment was carried out at least twice in triplicate.

Thus, 1 tripeptide according to the invention was tested, at a concentration of 50 nM, on the induction of cAMP, which was calculated with respect to the response of cAMP production induced by α-MSH (50 nM). The results are given in table 2 below.

TABLE 2 cAMP induction by the tripeptides according to the invention (given as a percentage of the maximum response with control peptide (1) at 50 nM) on a Cloudman S91 mouse melanoma cell line

| No. of peptide conjugate according to the invention | Structure | % cAMP induction |
|---|---|---|
| 1 | Palm-His-(D)Phe-Arg-$NH_2$ | 147 |

Determination of the $EC_{50}$:

The curves were adjusted and the $EC_{50}$ values were determined with nonlinear regression in the GraphPad Prism (GraphPad software). Each $EC_{50}$ value was the mean of at least two sets of independent experiments.

Binding Studies: Determination of the $IC_{50}$

The binding affinity of α-MSH for $MC_1$—R was determined by means of competition studies with [$^{125}$I]-NDP-MSH. Transfected Cos-1 cells were incubated in Dulbecco's modified Eagle medium containing 0.2% of BSA and 0.3 mM of phenatroline buffer, for 24 hours. $10^5$ cells were plated out onto 24-well plates with a radiolabeled ligand at a concentration of $5.8 \times 10^{-11}$ M. After incubation for 2 hours at 24° C. with various concentrations of ligand, washes were performed and the radioactivity was measured.

The $EC_{50}$ values for 2 tripeptides according to the invention were brought together in table 3 below and compared with the $EC_{50}$ values for control peptide and for α-MSH.

TABLE 3

$EC_{50}$ values for two tripeptides according to the invention compared with α-MSH, on cAMP production in M4Be cells

| Compounds | Structure | Retention time (min) | $EC_{50}$ (nM) |
|---|---|---|---|
| α-MSH | Ac-Ser-Tyr-Ser-Met-Glu-His-Phe-Arg-Trp-Gly-Lys-Pro-Val-$NH_2$ | 1.09 | 8.10 |
| control peptide | Ac-Nle-Ala-His-(D)Phe-Arg-Trp-$NH_2$ | 1.14 | 4.00 |
| 1 | Palm-His-(D)Phe-Arg-$NH_2$ | 1.66 | 2.3 |
| 2 | Palm-His-(D)Phe-Trp-$NH_2$ | 2.07 | 17.3 |

The results are in agreement with those obtained with the Palm-tripeptide 1 [Palm-His-(D)Phe-Arg-$NH_2$] indicating 147% cAMP induction.

The most important and the most striking result is the activity of the palmitoylated tripeptides with respect to the $MC_1$ receptor. In this study, we have shown that palmitoylation of the C-terminal peptides of the α-MSH sequence resulted in compounds that are active with respect to the $MC_1$ receptor, inducing cAMP production. These molecules have only a part of that which is described in the literature as the minimal sequence of the α-MSH agonist sequence.

Interestingly, removal of the tryptophan residue gave rise to the tripeptide 1, which showed activity in the nanomolar range ($EC_{50}$=2.3 nM). The tripeptide 2, which lacks Arg, exhibited a lesser potency, with an $EC_{50}$ of 17.3 nM. These tripeptides are good lead molecules for designing potent α-MSH ligands that are active with respect to $MC_1R$. These results also indicate that the presence of a hydrophobic chain on the N-terminal end of the α-MSH analogs, particularly of a palmitoyl group, is an important structural element for activation of the $MC_1$ receptor for α-MSH.

What is claimed is:

1. A tripeptide conjugate corresponding to general formula I:

$$A-AA1-AA2-AA3-NH_2 \qquad I$$

in which
- A is a radical corresponding to palmitic acid,
- AA1, AA2 and AA3, which may be identical or different, and are, independently of one another, an amino acid chosen from His, Phe, Arg, and Trp, with the proviso that at least one of AA1, AA2 or AA3 is Phe,
- in the form of enantiomers or of diastereoisomers, and also mixtures thereof, including racemic mixtures.

2. The tripeptide conjugate as claimed in claim 1, wherein at least one of AA1, AA2 or AA3 is chosen from the group consisting of Arg, His or Trp.

3. The tripeptide conjugate as claimed in claim 1, wherein AA2 is DPhe.

4. The tripeptide conjugate as claimed in claim 1, wherein AA2 or AA3 is Arg.

5. The tripeptide conjugate as claimed in claim 1, wherein AA1 is His.

6. The tripeptide conjugate as claimed in claim 1, wherein it is chosen from:
  1) Palm-His-DPhe-Arg-NH$_2$, and
  2) Palm-His-DPhe-Trp-NH$_2$.

7. A cosmetic, dermatological or pharmaceutical composition, which contains a tripeptide conjugate as claimed in claim 1 and, optionally, a cosmetically or pharmaceutically acceptable excipient.

8. The tripeptide conjugate as claimed in claim 1, wherein at least one of AA1, AA2 or AA3 is DPhe.

* * * * *